United States Patent [19]
Vattikonda

[11] Patent Number: 6,137,038
[45] Date of Patent: Oct. 24, 2000

[54] INBRED CORN LINE SM4603

[75] Inventor: Mohan Vattikonda, Lakeside, Canada

[73] Assignee: Cargill Incorporated, Wayzata, Minn.

[21] Appl. No.: 09/311,089

[22] Filed: May 13, 1999

[51] Int. Cl.[7] ............................. A01H 5/00; A01H 1/04; A01H 5/10; C12N 5/04
[52] U.S. Cl. .................. 800/320.1; 800/275; 800/298; 435/412; 435/424
[58] Field of Search ................. 800/320.1, 275, 800/298, 271; 435/412, 424, 430

[56] References Cited

U.S. PATENT DOCUMENTS

| | | | |
|---|---|---|---|
| 4,581,847 | 4/1986 | Hibberd et al. | 47/58 |
| 5,484,956 | 1/1996 | Lundquist et al. | 800/205 |

OTHER PUBLICATIONS

Kamo et al., "Establishment and Characterization of Long-–Term Embryogenic Maize Callus and Cell Suspension Cultures", *Plant Science*, 1986, 45:111–117.

Vasil et al., "Plant Regeneration from Friable Embryogenic Callus and Cell Suspension Cultures of *Zea mays* L.", *J. Plant Physiol.*, 1986, 124:399–408.

Walter R. Fehr, *Principles of Cultivar Development*, vol. 2, *Crop Species*, MacMillan, New York, 1987, Ch. 8:249–294.

Phillips et al. "Cell/Tissue Culture and In Vitro Manipulation", In Corn and Corn Improvement, 3rd. Ed., ASA Publication, #18, pp. 345–349 & 356–357, 1988.

*Primary Examiner*—Gary Benzion
*Assistant Examiner*—Melissa L. Kimball
*Attorney, Agent, or Firm*—Fish & Richardson, P.C., P.A.

[57] ABSTRACT

Inbred corn seed designated SM4603 and corn plants produced from that seed are disclosed. The invention includes plant parts from SM4603 corn plants. The invention includes a corn plant displaying all the physiological and morphological characteristics of a SM4603 corn plant, SM4603 pollen grains, plant parts, and tissue cultures. The invention also provides hybrid corn seed produced by crossing a SM4603 inbred corn plant with a second inbred corn plant.

7 Claims, No Drawings

INBRED CORN LINE SM4603

FIELD OF THE INVENTION

The invention relates to genetics, plant physiology, agronomy, corn breeding and inbred corn lines.

BACKGROUND OF THE INVENTION

Corn (*Zea mays* L.) is a monoecious plant, i.e., the male and female flowers develop on the same plant. They are located on the tassel and ear, respectively. Each silk on the ear represents an individual female flower, and each kernel represents a separate pollination event. Natural pollination occurs when pollen falls from the tassel onto the silk of the same plant, or is carried by wind from the tassel of one plant to the silk of a neighboring plant.

Corn breeders have employed controlled pollination, artificial selection, and genetic analysis to develop numerous genetic lines or varieties of corn that display desired traits such as yield potential, maturity time, disease resistance, insect resistance, ear size, plant height, drought tolerance. Established lines have been used as starting material for further rounds of crossing, selection, and analysis, to develop new and different varieties that display enhancement of particular traits or new combinations of traits. See, for example, Principles of Cultivar Development, Vol. 1, Fehr, W. ed. pp. 315–376, Macmillan, New York (1982).

The totality of the observable traits of a corn plant, i.e., the phenotype, results from the presence and interaction of many thousands of individual genetic loci. Each locus includes a pair of alleles, i.e., one from each parent. When a plant contains different alleles at a large number of loci, the plant is said to be heterozygous. In accordance with classical (Mendelian) genetics, a cross between two heterozygous plants yields a highly heterogeneous (nonuniform) population of offspring. Thus, heterozygous plants are not "true-breeding." However, crosses of heterozygous plants are useful starting material for creation of new inbred, i.e., highly homozygous, lines, which are true-breeding.

Creation of a new inbred line can begin with selection of individual lines or populations judged superior with respect to one or more traits of interest. The genetic backgrounds of the selected plants are combined by crossing to create a gene pool upon which selection for desired traits may be practiced. Selected progeny plants are self-pollinated and plants in the next generation that exhibit the desired phenotype(s) are selected from further selfing. This process can be repeated for several generations (typically 5–8 generations designated $F_1$, $F_2$, $F_3$, etc.), until the desired degree of homozygosity is achieved.

Pedigree breeding and recurrent selection breeding are two methods that can be used to develop inbred lines from breeding populations. Pedigree breeding typically begins with the crossing of two different genotypes, and superior plants are selfed and selected in successive generations. In pedigree breeding, five or more generations of selfing and selection typically is practiced. Recurrent selection breeding can be used to improve an inbred line, e.g., to transfer a specific desirable trait from one germplasm source to an inbred that lacks the trait.

Inbred lines, however made, typically display relatively poor growth and vigor. Nevertheless, two (or more) different inbred lines can be crossed to produce a heterozygous hybrid that displays growth and vigor superior to that of either inbred parent line. This phenomenon is known as hybrid vigor or heterosis. Because of hybrid vigor, practically all corn produced in the United States is grown from hybrid seeds. In some cases, hybrid seeds are produced from controlled crosses of three or even four different inbred lines.

SUMMARY OF THE INVENTION

The present invention provides inbred corn seed designated SM4603 (ATCC accession number 203445), and corn plants produced from that seed (SM4603 plants). The invention includes plant parts from SM4603 corn plants. The invention includes a corn plant displaying all the physiological and morphological characteristics of a SM4603 corn plant. The invention provides pollen grains from SM4603 corn plants. The invention includes a tissue culture derived from a SM4603 corn plant or derived from a SM4603 plant part. In some embodiments of the invention, the tissue culture yields regenerated plants having the genotype of inbred line SM4603 or displaying all the physiological and morphological characteristics of a SM4603 corn plant. The invention also provides hybrid corn seed produced by crossing a SM4603 inbred corn plant with a second inbred corn plant.

The invention also provides an $F_1$ hybrid corn plant produced by planting and growing seeds of a first corn inbred line designated SM4603 in pollinating proximity to seeds of a second corn inbred line, preventing pollen production on plants resulting from either the first or said second inbred line seeds, allowing cross pollination to occur between the plants of the inbred lines, harvesting seeds produced on the plants in which pollen production was prevented, and growing at least one of the harvested seeds.

Definitions

As used herein, corn plant "parts" means cells, protoplasts, tissue cultures from which corn plants can be regenerated, calli, plant clumps, embryos, pollen, flowers, kernels, ears, cobs, leaves, husks, stalks, roots, root tips, anthers, silk and other intact organs or tissues of a corn plant.

Heat Unit (GDU; growing degree unit) is calculated according to the following formula:

$$GDU=[(daily\ max\ temp)+(daily\ min\ temp)]/2-50$$

The basis of the formula is the following. Temperatures within the range of 50–86° F. are considered adequate for maize growth. Temperatures outside this range are not conductive to growth and are given a value of 50 or 86, respectively, for purposes of GDU calculation. GDUs are calculated from planting date on a daily basis. Cumulative values to certain growth stages are calculated.

Cotyledon Leaf Length is measured in centimeters at the three-leaf stage, and is classified as less than 5.5–7.5, or greater than 7.5 cm.

Plant Height is measured from the ground to the tip of the tassel, and is measured in centimeters (cm).

Ear Height is measured from the ground to the highest developed ear node attachment, in cm.

Stalk Diameter at the Second Node is measured after pollination and is given in cm.

Length of Top Ear is measured from the tip of the ear to the internode, and is measured in cm.

Ears is the average number of ears per plant.

Ear Leaf Width is the width of the leaf at the top ear node at its widest point, in cm.

No. Lvs Above Ear (number of leaves above the ear) is the number of leaves above the top ear node, classified as less than 5, 5–6, or more than 6.

Leaf Angle is the adaxial angle between the stalk and the second leaf above the ear, at anthesis and can be measured in degrees. Leaf angle can also be classified as V=very erect, U=upright, H=horizontal and D=drooping.

Leaf Sheath Pubesc (leaf sheath pubescence) is a visual measure of leaf hair density on the second leaf above the ear. It is rated on a scale from 1 to 9, with 1 being no leaf hair, and 9 being comparable to peach fuzz. It can also be classified as present or absent. A similar determination can be made for pubescence on the leaf margins.

Leaf Margin Waves is a visual measure of waviness at the edges of the leaves on the plant, and is measured on a scale of 1 to 9, with 1 being no waves, and 9 being many waves.

Total Number of Leaves is classified as less than 9, 10–15, or more than 15.

No. Prim. Lat. Branches (number of primary lateral branches on tassel) is the number of lateral tassel branches that originate from the central spike, classified as <4, 4–8, or >8 branches. Secondary Tassel Branches is the number of lateral tassel branches originating from primary lateral branches.

Tassel Extension is classified an enclosed, partially enclosed or open and is measured at mid-pollen shed.

Tassel Shed in Boot is classified as yes or no.

Tassel Difficulty in pulling is classified as easy, average, or hard.

Branch Angle is the adaxial angle between the central spike and the second primary lateral tassel branch from the top, an anthesis and is classified as <30, 30–60 or >60 degrees.

Tassel Length is the length of the tassel from the top leaf collar to the tassel tip, and is measured in cm. Lengths are classified as <25, 25–36, or >36 cm.

Tassel Number of Leaves Pulled is the average number of leaves removed when the tassel is removed by hand.

Plants, Tillering Tassel is the percentage of plants that have tillers which are shedding pollen and is measured at mid-pollen shed.

Pollen Shed is a visual measure of the amount of pollen shed by the tassel, and is rated on a scale of 1 to 9, with 1 being more (male sterile), and 9 being heavy shed.

Tassel Fertility is 9=Male Sterile, 7=Male Sterile, Anthers Extruded and No Pollen, 5=Intermediate With Some Viable and Nonviable Pollen, 3=Near Normal Pollen, 1=Completely Normal Pollen Shed and Viability Pollen Amount is measured as low, average, or heavy shed.

Tassel Attractiveness to Aphids is classified as Yes, Average or No.

Flowering Data is measured in GDU from planting to First Pollen shed and First Silk (10% of plants shedding pollen or in silk), Mid Pollen shed and Mid Silk (50% of plants shedding pollen or in silk) and Late Pollen shed and Late Silk (90% of plants shedding pollen or in silk).

Ear Leaves refer to leaf tips on the ear surface that extend outward from the surface and is classified as absent or present.

Husk Coverage is classified as short, covers tip, long, and is determined after drydown.

Husk Looseness refers to how readily husk leaves can be removed from the ear and is measured at drydown.

Ear Shank Length is classified as less than 10 cm, 10–30 cm or greater than 30 cm.

Ear Length is the length of the ear, from butt to tip, after husk removal, and is measured in cm. Ear length is classified as less than 15 cm, 15–23 cm or more than 23 cm.

Ear Shape is classified as cylindrical, conical or intermediate between cylindrical and conical (cylindrical/conical).

Mid Point Diam (mid point diameter) is a measure of the diameter of the ear, including kernels, midway along the length of the ear, after husk removal. It is measured in millimeters (mm).

Mid Cob Diam (mid cob diameter) is a measure of the diameter of the cob midway along its length, after husk and kernel removal. It is measured in millimeters (mm) and is classified as <25, 25–50, or >50.

Ear Weight is a measure of ear weight after drydown and husk removal, and is measured in grams (gm).

Ear Angle is measured at maturity as the angle between the stalk and position of the ear, and is scored on a scale of 1–9, with 1=dropping, 5=horizontal, 9=upright.

Kernel Rows is the average total number of kernel rows on the ear. If the rows are indistinct, this value is the average number of kernels located around the circumference of the ear at the mid-point of its length. Kernel rows are classified as 8–10, 12, 14, 16 or >18.

Kernel Type is classified as flint, semi-dent, dent or rough dent.

Kernel Length is measured in mm.

Kernel Width is measured in mm.

Kernel Thickness is measured in mm.

% Round Kernels is the percentage of round kernels in an unsized sample, using a $^{13}/_{64}$" slot screen.

100 K Wt is the weight of 100 kernels taken from an unsized sample, and is measured in gm.

% Dropped Ears is the percentage of plants whose ears have fallen to the ground at 65 days after anthesis.

% Root Lodging is the percentage of plants leaning at an angle greater than 30°, just before anthesis.

Yield Per Se is weight of kernels (measured at 12–13% grain moisture) per unit area of cultivated land, and is measured in kilograms per hectare (kg/ha).

NLB (northern leaf blight; *Exserohilum turcicum*) disease rating is scored visually on a scale of 1 to 9, with 9 indicating the highest disease resistance.

SLB (southern leaf blight; *Bipolar maydis*) disease rating is scored visually on a scale of 1 to 9, with 9 indicating the highest disease resistance.

NLS (northern leaf spot; *Exserohilum zeicola*) disease rating is scored visually on a scale of 1 to 9, with indicating the highest disease resistance.

GLS (gray leaf spot; *Cercospora zeae*) disease rating is scored visually on a scale of 1 to 9, with 9 indicating the highest disease resistance.

ES (eye spot; *Kabatiella zeae*) disease rating is scored visually on a scale of 1 to 9, with 9 indicating the highest disease resistance.

SWILT (Stewart's wilt; *Erwinia stewartii*) disease rating is scored visually on a scale of 1 to 9, with 9 indicating the highest disease resistance.

Color Code
  01—Light Green; 02—Medium Green; 03—Dark Green; 04—Very Dark Green; 05—Green-Yellow; 06—Pale Yellow; 07—Yellow; 08—Yellow-Orange; 09—Salmon; 10—Pink-Orange; 11—Pink; 12—Light Red; 13—Cherry Red; 14—Red; 15—Red & White; 16—Pale Purple; 17—Purple; 18—Colorless; 19—White; 20—White Capped; 21—Buff; 22—Tan; 23—Brown; 24—Bronze; 25—Variegated; 26—Other.

Stay Green is a visual rating of the color of the plant at 65 days after anthesis. The rating scale is from 1 to 9, with 1 being the worst stay green capacity (early die-back), and 9 being the best stay green capacity (late die-back).

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Seeds of the inbred corn line designated SM4603 were deposited on Nov. 9, 1998, in the American Type Culture Collection (ATCC), Manassas, Va. 20852 U.S.A. The ATCC Accession No. 203445. The deposited seeds were from the deposit maintained by Cargill, Inc., Wayzata, Minn. since prior to the filing date of this application. The ATCC deposit of inbred line SM4603 will be maintained without restriction in the ATCC depository for a period of 30 years, or five years after the most recent request, or for the effective life of the patent, whichever is longer. The deposit will be replaced if it becomes non-viable during that period. In making the SM4603 deposit, applicants have satisfied all the requirements of 37 C.F.R. §§ 1.801–1.800.

Inbred corn line SM4603 is a yellow dent corn (maize) inbred that is useful as one parent to produce $F_1$ hybrid corn. SM4603 is particularly suited for use as the male parent to produce single cross $F_1$ hybrid seed corn. Inbred line SM4603 is adapted to northern climates, including northern regions of North Dakota, Minnesota and Wisconsin, as well as regions of Canada, including Ontario. It can be used to produce hybrids of an average relative maturity of 80 to 90 days, based on the Comparative Relative Maturity Rating System for harvest moisture of grain. As an inbred per se, SM4603 is average yielding, with upright leaves and yellow dent kernels. It contributes rapid drydown and provides good stalk characteristics and average root characteristics. Hybrids involving SM4603 have high yields for maturity in high yield environments.

SM4603 shows uniformity and stability within the limits of environmental influence for the traits described in the data tables below. The SM4603 inbred line has been self-pollinated and ear-rowed for a sufficient number of generations to ensure sufficient homozygosity and phenotype stability for use in commercial production. SM4603 has been increased in appropriately isolated fields, under observation for uniformity, according to methods accepted in the corn seed industry. No significant variant traits have been observed in SM4603.

Inbred line SM4603 can be propagated by conventional plant breeding methods. SM4603 corn plants are grown to maturity under self-pollinating or sib-pollinating conditions with adequate isolation from corn plants of other genotypes. The resulting seeds are harvested and stored under conditions of suitable temperature and humidity.

In addition to propagation by conventional plant breeding methods, inbred corn line SM4603 can be maintained, manipulated, genetically transformed, or propagated by means of corn tissue culture. Techniques suitable for producing corn tissue cultures from inbred line SM4603, and regenerating fertile SM4603 corn plants from the tissue cultures are known in the art. Corn tissue culture techniques are described in numerous references, e.g., Hibberd et al, U.S. Pat. No. 4,581,847; Kamo et al., "Establishment and Characterization of Long-Term Embryogenic Maize Callus and Cell Suspension Cultures," Plant Science 45:111–117 (1986); Vasil et al., "Plant Regeneration from Friable Embryogenic Callus and Cell Suspension Culture of Zea mays L.," J. Plant Physiol. 124:399–308 (1986).

Inbred corn line SM4603 can be used as starting material for production of transgenic corn plants. Methods for producing transgenic corn plants are available to those of ordinary skill in the art. For an illustrative example of production of transgenic corn plants, see, e.g., U.S. Pat. No. 5,484,956. Examples of transgenes that can be introduced into corn line SM4603 include those conferring herbicide resistance, insect resistance, disease resistance, improved amino acid content of seed storage proteins, and improved nutritional quality of seed oil.

A substantially uniform assemblage of $F_1$ hybrid corn seed can be prepared using SM4603 as one parent. Such hybrid seeds can be conditioned and bagged in packaging material by means known in the art to form an article of manufacture. Such a bag of seed preferably has a package label accompanying the bag, e.g., a tag or label secured to the packaging material, a label printed on the packaging material or a label inserted within the bag. The package label indicates that the seeds therein are effective for producing corn grain.

Hybrid seed typically is purchased by growers, who then plant and cultivate the seed according to standard agronomic practices in the geographic area to which the hybrid is adapted. Growers will also typically take into account soil fertility, crop rotation practices and other factors specific to the locale in which the hybrid corn is being grown.

Inbred SM4603, and grain produced by employing inbred line SM4603, can be used as human food, livestock feed, and as raw material in industry. In addition to direct consumption of corn as food, corn-derived food products can be produced by industrial methods of dry-milling or wet-milling. Exemplary products of corn dry milling are grits, meal and flour. Exemplary products of wet-milling are corn starch, corn syrup, and dextrose for food use. Corn oil is obtained from corn germ, which is a by-product of both the dry- and wet-milling industries. Grain and non-grain portions of the corn plant, can be used as livestock feed, e.g., for beef cattle, dairy cattle, hogs, and poultry.

In addition to food uses, corn of the invention can be used in non-food, industrial applications. For example, grain can be used to produce corn starch or corn flour for non-food, industrial applications. These applications depend on functional properties, such as viscosity, film formation, adhesive properties, and ability to suspend particles. Corn starch and corn flour are useful, e.g., in the paper industry and textile industry. Corn of the invention also can be used industrially in adhesives, building materials, foundry binders, laundry starches, explosives, oil-well muds, and other mining applications. In addition to grain, other SM4603 corn plant parts are useful in industry. Stalks and husks can be processed into paper or wallboard. Cobs can be used for fuel or to make charcoal.

The characteristics of inbred maize line SM4603 are summarized and compared in Table 1 below to characteristics of a reference inbred designated herein as IH229.

TABLE 1

Characteristics of SM4603

|  | SM4603 | IH229 |
|---|---|---|
| COTYLEDON LEAF | | |
| Anthocyanin | Absent | N/A |
| Length | <5 | N/A |
| PLANT AND STALK | | |
| Anthocyanin in Brace Roots | Present | Absent |
| Anthocyanin in Nodes | Present | Absent |
| Stalk Diameter 2nd Node | 2.5 | 2.5 |
| LEAVES | | |
| Leaf Angle | U | V |
| Leaf Color | Variegated (light green) | 02 |
| Total Leaves | 10–15 | 10–15 |
| Leaves Above Ear | 5–6 | 5–6 |
| Ear Leaf Length | 22 | 22 |
| Ear Leaf Width (Max) | 9 | 8 |
| Anthocyanin, Margin | Absent | Absent |
| Anthocyanin, Sheath | Present | Absent |
| Pubescence, Margin | Present | Absent |
| Pubescence, Sheath | Present | Absent |
| Plants, Tillering Tassel % | 0 | 0 |
| TASSEL | | |
| Tassel Branch Angle | 30–60 | <30 |
| Tassel Branches, Primary | 4–8 | 4–8 |
| Secondary Tassel Branches | Absent | Absent |
| Tassel Length | 25–36 | 25–36 |
| Tassel Size | 5 | 5 |
| Tassel Shed in Boot | No | No |
| Tassel Extension | PE | E |
| Tassel Fertility | Normal | 0 |
| Tassel Leaves Pulled | 2 | 2 |
| Tassel Difficulty Pulling | Average | Hard |
| Anther Color | 07 | 07 |
| Glume Tip Color | 01 | 01 |
| Glume Base Color | 01 | 01 |
| Glume Band Color | N/A | 03 |
| Pollen Duration | Average | Short |
| Pollen Amount | Average | |
| EAR CHARACTERISTICS | | |
| Silk Color | 02 | 02 |
| Ear Leaves | Absent | Absent |
| Husk Coverage | Long | Short |
| Husk Looseness | Average | Average |
| Ear Angle | 8 | 7 |
| Shank Length | 10–30 | <10 |
| Ear Length | 15–23 | 15–23 |
| Ear Shape | Cy | CyCo |
| Kernel Rows | 8–10 | 10 |
| Kernel Type | Dent | Semi-dent |
| Kernel Body Color | 07 | 07 |
| Kernel Crown Color | 07 | 07 |
| Cob Color | 14 | 14 |
| Cob Diameter (midpoint) | <25 | <25 |
| Attractive to Aphids | No | No |

Table 1 provides a description of SM4603 and one of its parents, IH229. The leaves of SM4603 are of a dark green color at a medium angle with very strongly recurved leaves. The blade is medium in length (about 60 cm), but is very wide (about 10.5 cm). The SM4603 is characterized by a high total number of leaves (about 17) with many leaves above the ear (about 6). SM4603 plants are medium in length (about 190 cm) with ears inserted at about 75 cm. The ratio of height of ear to plant is medium. Anthocyanin is absent or very weak in internodes, nodes and sheath, but medium is brace roots.

The tassels of SM4603 are long and of medium compactness, with few primary branches. Lateral branches are very strongly recurved. The angle/main axis and branches are small. Coloration of the glume (tip to base) is absent or very weak. The main axis/lowest side branch is medium in length (about 30 cm), whereas the length of main axis/upper side branch is very long (about 30 cm). Male flowers appear at about 1000 GDUs. Silks emerge at a similar time. Coloration is absent or very weak in the anthers, while coloration is present in the silks. Intensity of coloration is very weak.

The ears of SM4603 are slightly recurved with long peduncles. Husk length is characterized as medium. The number of ear rows is small (about 8–10). The grain is uniform in shape, and yellow in color at the top of the grain and yellow-orange on the dorsal side. Kernel size is large. The glumes of the cob have weak coloration. The length (about 15 cm) and diameter (35 mm) of the ears is considered to be medium. The cob diameter is small (about 20 mm).

Hybrids having SM4603 as a male parent have deep and big kernels with good test weights. Such hybrids can be grown at high densities, with excellent yield and moisture characteristics.

Table 2 contain hybrid performance data comparing single cross hybrid HW712 with several commercial hybrids over three years. The male parent of HW712 is SM4603. In comparison with a hybrid designated HF555, HW712 had a lower yield, slightly more harvest moisture, has slightly less stalk lodging, slightly more root lodging, and slightly lower harvest moisture. When tested against a hybrid designated HU091, hybrid HW712 was higher yielding, had lower harvest moisture, had less stalk lodging, less root lodging, and higher test weight. The comparison with a hybrid designated HL057 showed a slight yield advantage for HW712, similar harvest moisture, less stalk lodging, similar root lodging, and slightly higher test weights. In a comparison with a hybrid designated HO510, hybrid HW712 was significantly higher yielding, was slightly higher in moisture, had less stalk lodging and less root lodging, and similar test weight.

TABLE 2

| Hybrid | Plots | Root Ldg % | Stalk Brk % | Harv Mst % | Test Wt | Yield* |
|---|---|---|---|---|---|---|
| HW712 | 63 | 0.5 | 2.0 | 21.4 | 55.5 | 134.8 |
| HF555 |  | 0.4 | 2.2 | 22.0 | 56.7 | 140.8 |
| HW712 | 7 | 0.7 | 2.5 | 20.5 | 55.4 | 141.9 |
| HU091 |  | 1.7 | 6.8 | 25.7 | 53.0 | 138.5 |
| HW712 | 28 | 0.9 | 1.7 | 22.7 | 55.5 | 142.3 |
| 3893 |  | 0.8 | 4.2 | 22.9 | 54.5 | 141.7 |
| HW712 | 41 | 0.6 | 2.4 | 22.7 | 54.4 | 134.9 |
| HO510 |  | 1.9 | 3.6 | 21.5 | 54.0 | 127.1 |

*Yield adjusted to 15.0% harvest moisture.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An inbred corn seed designated SM4603, represented by SM4603 seed deposited as ATCC accession number 203445.

2. A corn plant produced from the seed of claim 1.

3. A plant part of the plant of claim 2.

4. A pollen grain of the plant of claim 2.

5. A tissue culture derived from the corn plant of claim 2.

6. An $F_1$ hybrid corn seed produced by crossing a first corn inbred plant designated SM4603 and represented by SM4603 seed having ATCC Accession No. 203445 with a second inbred plant.

7. A corn plant grown from the $F_1$ hybrid corn seed of claim 6.

* * * * *